(12) United States Patent
Kishimoto et al.

(10) Patent No.: US 6,458,737 B1
(45) Date of Patent: Oct. 1, 2002

(54) CATALYST FOR OXIDIZING METHYLBENZENES AND METHOD FOR PRODUCING AROMATIC ALDEHYDE

(75) Inventors: Nobuji Kishimoto, Himeji; Isao Nakamura, Ikoma; Yusei Nagamura, Nishinomiya; Akiyoshi Nakajima, Akashi; Masashi Hashimoto, Himeji; Kunika Takahashi, Kakogawa, all of (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/709,276

(22) Filed: Nov. 13, 2000

(30) Foreign Application Priority Data

Nov. 10, 1999 (JP) .......................................... 11-319113

(51) Int. Cl.⁷ .......................... B01J 31/00; C07C 45/00; C07C 31/13
(52) U.S. Cl. ...................... 502/113; 568/431; 568/432; 568/434; 568/831; 568/833
(58) Field of Search .......................... 502/113; 568/431, 568/432, 434, 831, 833

(56) References Cited

U.S. PATENT DOCUMENTS

| | | | |
|---|---|---|---|
| 3,821,324 A | 6/1974 | Bertus | 260/680 E |
| 3,845,137 A | 10/1974 | Magder | |
| 4,017,547 A | 4/1977 | Simmons et al. | |
| 4,140,722 A | 2/1979 | Williams et al. | 260/599 |
| 4,374,270 A | 2/1983 | Ruszalla et al. | 562/599 |
| 5,324,702 A | 6/1994 | Yoo et al. | |

FOREIGN PATENT DOCUMENTS

| | | |
|---|---|---|
| EP | 0 724 908 | 8/1996 |
| EP | 0 958 860 A2 | 11/1999 |
| EP | 0 958 860 A3 | 11/1999 |
| GB | 1332831 | 10/1973 |
| JP | 48-97830 | 12/1973 |
| JP | 52000242 | 1/1977 |
| JP | 47-2086 | 1/1992 |
| JP | 11335311 | 12/1999 |

Primary Examiner—Sreeni Padmanabhan
Assistant Examiner—Sikarl A. Witherspoon
(74) Attorney, Agent, or Firm—Connolly Bove Lodge & Hutz LLP

(57) ABSTRACT

The present invention has for its object to provide a novel catalyst by use of which methylbenzenes can be oxidized in gaseous phase in the presence of molecular oxygen to give the corresponding aromatic aldehydes in high yields, a process for producing an aromatic aldehyde from the corresponding methylbenzene in a high yield by use of said catalyst, and a process for producing cyclohexanedimethanol which comprises hydrogenating phthalaldehyde among the aromatic aldehydes which can be obtained as above.

The present invention is directed to a catalyst for oxidation of methylbenzene
which is used for the production of the corresponding aromatic aldehyde by the gas-phase oxidation of a methylbenzene in the presence of molecular oxygen,
and has a composition of the following general formula (1):

$$W_a X_b Y_c O_x \qquad (1)$$

wherein W represents a tungsten atom; X represents at least one kind of element selected from the group consisting of P, Sb, Bi and Si; Y represents at least one element selected from the group consisting of Fe, Co, Ni, Mn, Re, Cr, V, Nb, Ti, Zr, Zn, Cd, Y, La, Ce, B, Al, Tl, Sn, Mg, Ca, Sr, Ba, Li, Na, K, Rb and Cs; O represents an oxygen atom; a, b, c and x represent the numbers of atoms of W, X, Y and O, respectively; provided, however, the proportions of a, b and c are such that when a=12, b=0.5 to 10 and c=0 to 15; X represents a numerical value which is determined by the oxidized states of the elements other than oxygen.

10 Claims, No Drawings

CATALYST FOR OXIDIZING METHYLBENZENES AND METHOD FOR PRODUCING AROMATIC ALDEHYDE

TECHNICAL FIELD

The present invention relates to a catalyst for use in the oxidation of methylbenzenes, a process for producing aromatic aldehydes by use of said catalyst, and further a process for producing cyclohexanedimethanol from the phthalaldehyde so produced. More particularly, the present invention relates to a catalyst suited for the gas-phase oxidation of a methylbenzene in the presence of molecular oxygen to give the corresponding aromatic aldehyde in high yield, a process for oxidizing a methylbenzene in gaseous phase in the presence of molecular oxygen by use of said catalyst to produce the corresponding aromatic aldehyde in high yield, and further a process for hydrogenating the phthalaldehyde so produced to give cyclohexanedimethanol.

BACKGROUND ART

Aromatic aldehydes have highly reactive aldehyde groups and, among all aromatic compounds, are particularly broad in the spectrum of applicability. Terephthalaldehyde (TPAL), in particular, which has two aldehyde groups in para-positions, is a promising material to be exploited in the production of pharmaceutical products, agrochemicals, dyestuffs, liquid crystal polymers, electrically conductive polymers, and heat resistant plastics, among other uses, and there is a demand for development of an uncostly technology for the production of TPAL.

The first attempt to produce terephthalaldehyde by the gas-phase oxidation of p-xylene dates back to a fairly long time ago. Japanese Kokoku Publication Sho-47-2086 discloses an oxide catalyst composed of W and Mo in a ratio of 1:1 to 20:1. Japanese Kokai Publication Sho-48-47830 discloses a catalyst comprising V and either Rb or Cs. U.S. Pat. No. 3,845,137 discloses a catalyst composed of the two elements of W and Mo plus at least one element selected from the group consisting of Ca, Ba, Ti, Zr, Hf, Tl, Nb, Zn and Sn. U.S. Pat. No. 4,017,547 discloses a catalyst composed of Mo oxide, either W oxide or silicotungstic acid, and Bi oxide. U.S. Pat. No. 5,324,702 describes a special catalyst comprising Fe, Zn, V, Mo and W as supported by chemical vapor deposition (CVD) on deboronized borosilicate crystal molecular sieves.

However, these catalysts are invariably unsatisfactory in the production yield of the objective product terephthalaldehyde and none have been exploited with success on a commercial scale.

Furthermore, the investigations of the inventors proved that these catalysts lead to contain impurities causing the decrease in the yield of 1,4-cyclohexanedimethanol due to its low activity and its low selectivity for the objective compounds in hydrogenation of the obtained terephthalaldehyde.

Meanwhile, cyclohexanedimethanol is an industrially useful compound as a starting material for the production of polyester series coatings, synthetic fibers and synthetic resins, among other products.

The hitherto-known production technology for 1,4-cyclohexanedimethanol includes (1) the process starting with a dialkyl terephthalate which comprises hydrogenating the benzene ring of the dialkyl terephthalate ester and further hydrogenating the resulting 1,4-cyclohexanedicarboxylate dialkyl ester, (2) the process starting with terephthalic acid which comprises hydrogenating its benzene ring in the same manner as above and further hydrogenating the resulting 1,4-cyclohexanedicarboxylic acid, (3) the process which comprises hydrogenating the benzene ring of xylylene glycol, and (4) the process which comprises hydrogenating terephthalaldehyde.

The most representative of these processes is the process (1). However, the dialkyl terephthalate used as the starting material is synthesized by oxidizing p-xylene and esterifying the resulting terephthalic acid with an alcohol and in order to obtain the objective compound, the ester must be further subjected to two steps of hydrogenation. Thus, this process requires a multiple-reaction scheme.

In the process (2), where the starting material is terephthalic acid which can be obtained by oxidizing p-xylene, no esterification reaction is required but as pointed out in Japanese Kokai Publication Sho-52-242, the hydrogenation involves the use of a large amount of alcohol as the solvent, thus causing the disadvantage of low productivity.

Furthermore, in these processes, high-temperature, high-pressure conditions are required for the hydrogenation of the benzene ring and the carboxylic acid or its ester and, hence, the use of a special reaction equipment is essential. In addition, the copper chromite catalyst used in the later-stage reaction contains chromium which is poisonous so that a disposal problem is inevitable.

In these reactions, stoichiometrically 7 moles of hydrogen is required per mole of the substrate compound and, hence, a large amount of hydrogen is consumed. Furthermore, since 2 moles of alcohol is formed as a byproduct in the process (1) and 2 moles of water in the process (2), the amounts of starting materials required for unit production are also large. Therefore, these processes cannot necessarily be considered to be satisfactory from economic points of view.

Referring to said process (3), Japanese Kokai Publication Hei-8-187432, for instance, discloses, in the section of Example 7, a process for obtaining the objective compound cyclohexanedimethanol by hydrogenating the benzene ring of xylylene glycol using a novel hydrogenation catalyst, i.e. the Raney ruthenium catalyst, under mild conditions.

In this process, however, the starting material xylylene glycol is very expensive, and an inexpensive commercial production technology remains to be established as yet.

Japanese Kokai Publication Hei-11-335311, recently laid open for public inspection, discloses a process corresponding to said process (4), that is a one-step hydrogenation reaction process, which comprises hydrogenating the aldehyde groups and the benzene ring of terephthalaldehyde concurrently using a catalyst comprising metals of the group VIII of the long-form periodic table under defined relatively mild conditions.

This process requires hydrogenation of both the aldehyde groups and the benzene ring but stoichiometrically only 5 moles of hydrogen is required per mole of the substrate and there is no by-production of alcohol or water. In addition, the process does not require a catalyst containing a poisonous component.

However, in regard of this process, too, a commercial production technology for the starting material terephthalaldehyde has not been established as yet and the above patent literature does not allude to any specific procedure for producing terephthalaldehyde.

SUMMARY OF THE INVENTION

In view of the above state of the art, the present invention has for its object to provide a novel catalyst by use of which methylbenzenes can be oxidized in gaseous phase in the presence of molecular oxygen to give the corresponding aromatic aldehydes in high yields, a process for producing an aromatic aldehyde from the corresponding methylbenzene in a high yield by use of said catalyst, and a process for producing cyclohexanedimethanol which comprises hydrogenating phthalaldehyde among the aromatic aldehydes which can be obtained as above.

The inventors of the present invention made an intensive search for a novel catalyst with which an aromatic aldehyde may be produced in high yield by oxidizing the corresponding methylbenzene in gaseous phase in the presence of molecular oxygen and found that a catalyst having the composition described hereinafter or a catalyst comprising the catalyst active species as supported on a fire-resistant inorganic carrier has excellent partial oxidizing activity and that by using this catalyst, the object aromatic aldehyde can be produced in good yield. The inventors further found that by hydrogenating phthalaldehyde in particular, among the aromatic aldehydes which can thus be obtained, cyclohexanedimethanol can be produced with high efficiency. The present invention has its base on the above findings.

DETAILED DESCRIPTION OF THE INVENTION

The term "methylbenzene" is used herein to mean any compound having one or a plurality of methyl groups directly joined to the benzene ring, and as representative examples of the methylbenzene, there can be mentioned methylbenzenes each containing 8 to 10 carbon atoms such as p-xylene, o-xylene, m-xylene, psudocumene, mesitylene, and durene.

The catalyst of the present invention catalyzes the gas-phase oxidation reaction of methylbenzenes in the presence of molecular oxygen to give the corresponding aldehydes. To be specific, there can be mentioned the production of terephthalaldehyde and p-tolualdehyde from p-xylene; phthalaldehyde and o-tolualdehyde from o-xylene; isophthalaldehyde and m-tolualdehyde from m-xylene; 2-methylterephthalaldehyde, 2,4-dimethylbenzaldehyde, 2,5-dimethylbenzaldehyde, and 3,4-dimethylbenzaldehyde from pseudocumene; 3,5-dimethylbenzaldehyde, 5-methylisophthalaldehyde and 1,3,5-triformylbenzene from mesitylene; and 2,5-dimethylterephthalaldehyde, 4,5-dimethylphthalaldehyde, 2,4,5-trimethylbenzaldehyde, 2,4,5-triformyltoluene and 1,2,4,5-tetraformylbenzene from durene; among others. Particularly, the oxidation catalyst of the present invention finds application, with particular advantage, in the production of terephthalaldehyde from p-xylene.

The catalyst for oxidation of methylbenzene of the present invention has a composition of the following general formula (1):

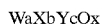

$W_a X_b Y_c O_x$              (1).

In the general formula (1), W represents a tungsten atom; X represents at least one kind of element selected from the group consisting of P, Sb, Bi and Si; Y represents at least one element selected from the group consisting of Fe, Co, Ni, Mn, Re, Cr, V, Nb, Ti, Zr, Zn, Cd, Y, La, Ce, B, Al, Tl, Sn, Mg, Ca, Sr, Ba, Li, Na, K, Rb and Cs; O represents an oxygen atom.

Referring further, to the above general formula (1), the preferred element among said P, Sb, Bi and Si for X is Sb and/or Bi, with Sb being particularly preferred. Among Fe, Co, Ni, Mn, Re, Cr, V, Nb, Ti, Zr, Zn, Cd, Y, La, Ce, B, Al, Tl, Sn, Mg, Ca, Sr, Ba, Li, Na, K, Rb and Cs as mentioned for Y, Y is preferably at least one element selected from the group consisting of Fe, Co, Ni, Mn, Zn, Cr, Cd, V, Nb, Ti, Zr, Ce, Sr and Cs, more preferably at least one element selected from the group consisting of Fe, Ni, Co, Zn, Cd and Mn.

Further, in the general formula (1), a, b, c and x represent the numbers of atoms of W, X, Y and oxygen, respectively; provided, however, that the proportions of a, b and c are such that when a=12, b=0.5 to 10 and c=0 to 15 and x is a numerical value determined by the oxidized states of the elements other than oxygen.

The proportions of a, b and c are preferably such that when a=12, b=1 to 6 and c=0 to 8 and x is a numerical value determined by the oxidized states of the elements other than oxygen. The case of a=12 is taken here for merely illustrating the proportions of a, b and c, and when the value of a assumes a different number, the values of b and c are changed accordingly.

The oxidation catalyst of general formula (1) according to the present invention may be used as supported on a fire-resistant inorganic carrier for enhanced activity and improved physical endurance. The above fire-resistant inorganic carrier includes the fire-resistant inorganic carriers in common use for the preparation of catalysts of this type. As typical examples, alumina, e.g. α-alumina, silica, titania, zirconia, silicon carbide, etc. can be mentioned. Particularly, low-specific-surface-area α-alumina and silicone carbide each having a specific surface area of not more than 1 $m^2/g$, preferably not more than 0.1 $m^2/g$, are preferred because the risk for side reactions is low and the object compound can be obtained in high yield. The amount of the catalyst active species to be supported is usually 5 to 90 mass % based on the fire-resistant inorganic carrier.

The method of preparing the oxidation catalyst of the present invention is not particularly restricted but the objective catalyst can be prepared by the technology which is used generally in the production of catalysts of this type. A typical method comprises adding an aqueous solution of antimony tartrate or a powder of antimony trioxide, as well as an aqueous solution of iron nitrate, to an aqueous solution of ammonium metatungstate to prepare a homogeneous solution or suspension, immersing a molded carrier in said solution or suspension, evaporating the water off to dryness, subjecting the residue to drying at 80 to 230° C. and calcining at 300 to 700° C. In the case of not using the carrier, said solution or suspension is subjected to directly heating with stirring, followed by drying at the above temperature, pulverizing, molding and calcining at the above temperature. The atmosphere in which the above drying and calcining is carried out is not particularly restricted. Thus, these operations can be carried out in any of an oxygen-rich or oxygen-lean atmosphere, a reducing atmosphere, or an inert gas atmosphere such as nitrogen, helium or argon gas, or even in vacuo. A suitable kind of atmosphere can be judiciously selected according to characteristics of the raw materials used in the preparation of the catalyst. Compared with calcining in the atmospheric air, calcining in an oxygen-lean atmosphere tends to result in a decrease in catalyst activity but, in certain cases, leads to improvements in selectivity and yield. When solid powdery oxide materials are used, calcining in an inert gas atmosphere is particularly preferred. The raw materials for use in the preparation of the catalyst are not particularly restricted but there can be used the nitrate, sulfate, oxide, hydroxide, chloride, carbonate, organic acid salt, oxygen acid, oxygen acid ammonium salt, heteropolyacid, etc. of the element to be used can be employed.

The shape of the fire-resistant inorganic carrier for use in the preparation of the supported catalyst is not particularly restricted, either. For example, not only molded products but also oxide or hydroxide powders, gels, sols, and so on can be selectively used according to the conditions of use of the catalyst. The shape of the catalyst is not particularly restricted, either, but spheres, pellets, rings, a honeycomb, etc. can be selectively used.

Referring to the above technology for producing aromatic aldehydes which comprises oxidizing the corresponding methylbenzenes in gaseous phase in the presence of molecular oxygen, the process for producing an aromatic aldehyde by use of the catalyst for oxidation of methylbenzene described above is also one aspect of the present invention and an aromatic aldehyde can be produced from the corresponding methylbenzene in high yield by this process.

The present invention is also related to a process for producing an aromatic aldehyde comprising oxidizing the corresponding methylbenzene in gaseous phase in the presence of molecular oxygen, that is to say a process for producing the aromatic aldehyde by use of said catalyst for oxidation of methylbenzene.

The methylbenzene as a starting material in the above process for producing an aromatic aldehyde is not particularly restricted but is preferably a methylbenzene containing 8 to 10 carbon atoms, for instance.

The above methylbenzene containing 8 to 10 carbon atoms includes the same compounds as mentioned hereinbefore. Among them, the process for producing an aromatic aldehyde according to this aspect of the invention is particularly suitable for the production of terephthalaldehyde by gas-phase oxidation of p-xylene.

In conducting the gas-phase oxidation reaction in accordance with this invention, a diluent gas can be used in addition to said methylbenzene and molecular oxygen. As the source of molecular oxygen, air or pure oxygen is employed. The molecular oxygen is generally used in a proportion of 5 to 100 moles per mole of the methylbenzene. The preferred diluent gas is an inert gas, such as nitrogen, helium, carbon dioxide and the like, or water vapor.

The reaction conditions for the gas-phase oxidation of the present invention are not particularly restricted but it is sufficient to bring the above material gas into contact with catalyst for oxidation of the invention, for example at a space velocity of 1000 to 100000 $hr^{-1}$ and a reaction temperature of 350 to 650° C. The preferred space velocity is 2000 to 50000 $hr^{-1}$ and the preferred reaction temperature is 450 to 600° C. The above reaction is usually carried out at atmospheric pressure or slightly elevated pressure, although it may be carried out at a high pressure or under reduced pressure. The reaction system is not particularly restricted, either, but may be a fixed bed system, a moving-bed system or a fluidized-bed system. It may also be a one-pass system or a recycling system.

The process for producing cyclohexanedimethanol which comprises hydrogenating the phthalaldehyde obtained by the above-described process for producing an aromatic aldehyde using xylene as the starting material methylbenzene also constitutes an aspect of the present invention, and by using this process, cyclohexanedimethanol can be produced from xylene at low cost on a commercial scale.

The process for producing 1,4-cyclohexanedimethanol which comprises hydrogenating the terephthalaldehyde obtained by the above-described process for producing an aromatic aldehyde also constitutes a further aspect of the present invention, and by using this process, 1,4-cyclohexanedimethanol can be produced from p-xylene at low cost on a commercial scale.

In the above process for producing cyclohexanedimethanol, the hydrogenation of phthalaldehyde can be carried out by any known technique. For example, there can be mentioned the standard method comprising causing the substrate to react with hydrogen in the presence of a reducing catalyst such as (I) a supported noble metal catalyst prepared by supporting a noble metal (platinum group), such as palladium, platinum, ruthenium, rhodium and iridium, on a carrier such as activated carbon, alumina, diatomaceous earth or the like; (II) a noble metal oxide such as palladium oxide, platinum oxide, ruthenium oxide, rhodium oxide, iridium oxide and the like; (III) a noble metal such as palladium black, platinum black, ruthenium black, rhodium black and the like; (IV) a Raney catalyst such as Raney nickel, Raney cobalt, Raney ruthenium and the like; or (V) a supported base metal catalyst prepared by supporting a base metal on a carrier.

In accordance with the present invention, phthalaldehyde of high purity is obtained in the first oxidation stage and this product may be used as it is without further purification. Of course, it may be purified, if desired.

The reaction temperature, hydrogen partial pressure and other conditions can be judiciously selected according to the kind and amount of reducing catalyst used, among other parameters, and are not particularly restricted. Generally speaking, the reaction temperature may range from room temperature to 250° C., preferably 50 to 200° C. If the reaction temperature deviates from the above range, the reaction tends to be remarkably retarded or side reactions such as a functional group-leaving reaction may take place to drastically reduce the selectivity of the reaction.

The hydrogen partial pressure is preferably not less than 1 MPa. When it is less than 1 MPa, the xylylene glycol, formed on reduction of only the aldehyde groups not reacted in the system, tends to remain in a large proportion. The hydrogenation may be carried out using a suspension of phthalaldehyde in an inert medium but is preferably carried out using a solution thereof in a suitable solvent such as an alcohol and ether. The mode of hydrogenation may be batchwise, semi-batchwise or continuous.

The catalyst for oxidation of methylbenzene according to the present invention has excellent partial oxidation activity and enables the production of aromatic aldehydes from the corresponding methylbenzenes in high yield.

Furthermore, by the process for producing cyclohexanedimethanol in accordance with the present invention, cyclohexanedimethanol which is of great value as a starting material for polyester coatings, synthetic fibers and synthetic resins can be produced from xylene, which is a readily available and inexpensive material, at low cost on a commercial scale.

BEST MODE FOR CARRYING OUT THE INVENTION

The following examples are further illustrative of the present invention. The conversion rate, selectivity and one-pass yield of the reaction, taking byproducts into account, are defined as follows.

Conversion rate (mole %)=(the number of moles of the reacted starting compound/the number of moles of the fed starting compound)×100

Selectivity (mole %)=(the number of moles of each product compound/the number of moles of the reacted starting compound)× (the number of carbon atoms of each product compound/the number of carbon atoms of the fed starting compound)×100

One-pass yield (mole %)=(the number of moles of each product compound/the number of moles of the fed starting compound)×(the number of carbon atoms of each product compound/the number of carbon atoms of the fed starting compound)×100

EXAMPLE 1

As the source of antimony, an aqueous solution of antimony tartrate was first prepared. In 310 ml of water was dissolved 150.0 g of L-tartaric acid followed by the addition of 36.5 g of antimony trioxide (purity 99.9%) powder, and the mixture was refluxed for dissolution. To the solution was added a small amount of water to make a total of 500 g, whereby an aqueous solution of antimony tartrate with an Sb concentration of 0.5 mmol/g was obtained. On the other hand, as the Fe source, an aqueous solution of iron nitrate was prepared. Thus, 40.4 g of iron nitrate.9H$_2$O was dissolved in water to make 100 g, whereby an aqueous solution of iron nitrate with an Fe concentration of 1 mmol/g was obtained. To 6.00 g of the above aqueous solution of antimony tartrate was added 2.00 g of this aqueous solution of iron nitrate, followed by addition of 5.56 g of ammonium metatungstate aq. sol. (50 mass % WO$_3$) to give a homogeneous impregnating liquor. To 20 g of the α-alumina support SA5218 (Norton, ⅜-inch sphere), preheated to 100° C., was added the above impregnating liquor and the mixture was heated with stirring on a water bath for evaporation to dryness. The residue was dried at 120° C. for 16 hours, and calcined in the atmospheric air at 650° C. for 2 hours. The free particles were dusted off to give a finished catalyst (the same applies to the following examples) which had a composition of 14.3 mass % W$_{12}$Sb$_3$Fe$_2$Ox/SA5218. The conventional flow reaction tube was packed with 20 g of the above catalyst and the reaction was conducted under the following conditions. The results are shown in Table 1.

Reaction pressure: atmospheric

Reactant gas composition: p-xylene/air=0.8/99.2 (p-xylene/O$_2$=1/25.8)

Reactant gas feed rate: 1.25 L (volume of gas at 0° C., 1.013×10$^{-1}$ MPa; normal state)/min.

SV: 5680 hr$^{-1}$

Reaction temperature: 550° C.

In the following examples, the reactions were carried out under the same reaction condition as far as not giving the limitation. It should be understood that SV may have varied slightly owing to the difference in the packed specific gravity of the catalyst (the same applies to the following examples). The temperatures and results of the reactions are shown in Table 1.

EXAMPLE 2

Except that the amount of the aqueous solution of antimony tartrate was adjusted to 8.00 g, the procedure of Example 1 was otherwise repeated to prepare a catalyst. The composition of this catalyst was 14.6 mass % W$_{12}$Sb$_4$Fe$_2$Ox/SA5218.

EXAMPLE 3

Except that the amount of the aqueous solution of antimony tartrate was adjusted to 4.00 g, the procedure of Example 1 was otherwise repeated to prepare a catalyst. The composition of this catalyst was 13.6 mass % W$_{12}$Sb$_2$Fe$_2$Ox/SA5218.

EXAMPLE 4

Except that the amount of the aqueous solution of iron nitrate was adjusted to 3.00 g, the procedure of Example 1 was repeated to prepare a catalyst. The composition of this catalyst was 14.6 mass % W$_{12}$Sb$_3$Fe$_3$Ox/SA5218.

EXAMPLE 5

Except that the amount of antimony tartrate was changed to 2.00 g and the amount of the aqueous solution of iron nitrate to 1.00 g, the procedure of Example 1 was faithfully followed to prepare a catalyst. The composition of this catalyst was 12.9 mass % W$_{12}$Sb$_1$Fe$_1$Ox/SA5218.

EXAMPLE 6

As the source of Zr, an aqueous solution of zirconyl nitrate was prepared. Thus, 13.50 g of zirconyl nitrate.2H$_2$O was dissolved in water to make 100 g, whereby an aqueous solution of zirconyl nitrate with a Zr concentration of 0.5 mmol/g was obtained. Using an impregnating liquor prepared by adding 1.0 g of this aqueous solution of zirconyl nitrate to the impregnating liquor used in Example 1, the procedure of Example 1 was otherwise repeated to prepare a catalyst. The composition of this catalyst was 14.4 mass % W$_{12}$Sb$_3$Fe$_2$Zr$_{0.5}$Ox/SA5218.

EXAMPLE 7

As the source of Cs, an aqueous solution of cesium nitrate was prepared. Thus, 9.75 g of cesium nitrate was dissolved in water to make 50 g, whereby an aqueous solution with a Cs concentration of 1 mmol/g was obtained. Using an impregnating liquor prepared by adding 0.5 g of the above aqueous solution of cesium nitrate to the impregnating liquor used in Example 1, the procedure of Example 1 was otherwise repeated to prepare a catalyst. The composition of this catalyst was 14.4 mass % W$_{12}$Sb$_3$Fe$_2$Cs0.5Ox/SA5218.

EXAMPLE 8

As the source of Nb, an aqueous solution of niobium oxalate was prepared. Thus, 12.97 g of niobium oxalate (20.5% as Nb$_2$O$_5$) was dissolved in water to make 100 g, whereby an aqueous solution of niobium oxalate with a Nb concentration of 0.1 mmol/g was obtained. Using an impregnating liquor prepared by adding 5.0 g of the above aqueous solution to the impregnating liquor used in Example 1, the procedure of Example 1 was otherwise repeated to prepare a catalyst. The composition of this catalyst was 14.4 mass % W$_{12}$Sb$_3$Fe$_2$Nb$_{0.5}$Ox/SA5218.

EXAMPLE 9

As the source of Bi, an aqueous solution of bismuth nitrate was prepared. Thus, 24.26 g of bismuth nitrate was dissolved in a solution prepared by diluting 20 g of 60% nitric acid with 50 g of water and made up with water to 100 g, whereby an aqueous solution of bismuth nitrate with a Bi concentration of 0.5 mmol/g was obtained. First, using 6.0 g of this bismuth nitrate solution alone as the impregnating liquor, the impregnation and evaporation procedure was carried out as in Example 1. Then, a further impregnation was carried out using a solution prepared by the aqueous solution of ammonium metatungstate and aqueous solution of iron nitrate as used in Example 1 (the amounts used are also the same as in Example 1), followed by the same drying and calcining operations as in Example 1. The composition of the catalyst thus obtained was 14.9 mass % W$_{12}$Bi$_3$Fe$_2$Ox/SA5218.

EXAMPLE 10

Using a solution prepared by dissolving 3.42 g of phosphotungstic acid H$_3$(PW$_{12}$O$_{40}$).nH$_2$O in 5 ml of water as an impregnating liquor, a catalyst was prepared as in Example 1. The composition of this catalyst was 12.8 mass % $W_{12}P_1Ox/SA5218$.

EXAMPLE 11

Using an impregnating liquor prepared by dissolving 2.84 g of silicotungstic acid ($SiO_2 \cdot W_{12}O_3 \cdot 26H_2O$) in 5 ml of water, a catalyst was prepared as in Example 1. The composition of this catalyst was 12.1 mass % $W_{12}Si_1Ox/SA5218$.

EXAMPLE 12

As the source of K, an aqueous solution of potassium nitrate was prepared. Thus, 5.06 g of potassium nitrate was dissolved in water to make 50 g, whereby an aqueous solution of potassium nitrate with a K concentration of 1 mmol/g was obtained. Using an impregnating liquor prepared by adding 0.5 g of this aqueous solution of potassium nitrate to the impregnating liquor used in Example 8, a catalyst was prepared in otherwise the same manner as in Example 1. The composition of this catalyst was 14.5 mass % $W_{12}Sb_3Fe_2Nb_{0.5}K_{0.5}Ox/SA5218$.

EXAMPLE 13

As the source of Co, an aqueous solution of cobalt nitrate was prepared. Thus, 14.64 g of cobalt nitrate.$6H_2O$ was dissolved in water to make 50 g, whereby an aqueous solution of cobalt nitrate with a Co concentration of 1 mmol/g was obtained. Using 3.00 g of this aqueous solution of cobalt nitrate in lieu of the aqueous solution of iron nitrate, increasing the amount of the aqueous solution of antimony tartrate to 9.00 g and the amount of the ammonium metatungstate aq. sol. to 8.34 g, and adjusting the calcining temperature to 600° C., a catalyst was prepared in otherwise the same manner as Example 1. The composition of the catalyst thus obtained was 17.1 mass % $W_{12}Sb_3Co_2Ox/SA5218$.

EXAMPLE 14

Except that the amount of the aqueous solution of cobalt nitrate was increased to 9.00 g, the procedure of Example 13 was repeated to prepare a catalyst. The composition of this catalyst was 16.7 mass % $W_{12}Sb_3Co_6Ox/SA5218$.

EXAMPLE 15

As the source of Ni, an aqueous solution of nickel nitrate was prepared. Thus, 14.55 g of nickel nitrate.$6H_2O$ was dissolved in water to make 50 g, whereby an aqueous solution of nickel nitrate with a Ni concentration of 1 mmol/g was obtained. Using 9.00 g of this aqueous solution of nickel nitrate in lieu of the aqueous solution of cobalt nitrate, a catalyst was prepared in otherwise the same manner as in Example 13. The composition of this catalyst was 15.4 mass % $W_{12}Sb_3Ni_6Ox/SA5218$.

EXAMPLE 16

As the source of Zn, an aqueous solution of zinc nitrate was prepared. Thus, 14.89 g of zinc nitrate.$6H_2O$ was dissolved in water to make 50 g, whereby an aqueous solution of zinc nitrate with a Zn concentration of 1 mmol/g was obtained. Using 9.00 g of this aqueous solution of zinc nitrate in lieu of the aqueous solution of cobalt nitrate, a catalyst was prepared in otherwise the same manner as in Example 13. The composition of this catalyst was 16.3 mass % $W_{12}Sb_3Zn_6Ox/SA5218$.

EXAMPLE 17

As the source of Cd, an aqueous solution of cadmium nitrate was prepared. Thus, 15.44 g of cadmium nitrate.$4H_2O$ was dissolved in water to make 50 g, whereby an aqueous solution of c nitrate with a Cd concentration of 1 mmol/g was obtained. Using 9.00 g of this aqueous solution of cadmium nitrate in lieu of the aqueous solution of cobalt nitrate, a catalyst was prepared in otherwise the same manner as in Example 13. The composition of this catalyst was 15.8 mass % $W_{12}Sb_3Cd_6Ox/SA5218$.

EXAMPLE 18

As the source of Mn, an aqueous solution of manganese nitrate was prepared. Thus, 14.37 g of manganese nitrate.$6H_2O$ was dissolved in water to make 50 g, whereby an aqueous solution of manganese nitrate with a Mn concentration of 1 mmol/g was obtained. Using 9.00 g of this aqueous solution of manganese nitrate in lieu of the aqueous solution of cobalt nitrate, a catalyst was prepared in otherwise the same manner as in Example 13. The composition of this catalyst was 12.7 mass % $W_{12}Sb_3Mn_6Ox/SA5218$.

EXAMPLE 19

As the source of Ca, an aqueous solution of calcium nitrate was prepared. Thus, 14.37 g of calcium nitrate.$4H_2O$ was dissolved in water to make 50 g, whereby an aqueous solution of calcium nitrate with a Ca concentration of 1 mmol/g was obtained. Using 3.00 g of this aqueous solution of calcium nitrate in lieu of the aqueous solution of cobalt nitrate, a catalyst was prepared in otherwise the same manner as in Example 13. The composition of this catalyst was 14.6 mass % $W_{12}Sb_3Ca_2Ox/SA5218$.

EXAMPLE 20

As the source of Sr, an aqueous solution of strontium nitrate was prepared. Thus, 10.69 g of strontium nitrate was dissolved in water to make 50 g, whereby an aqueous solution of strontium nitrate with a Sr concentration of 1 mmol/g was obtained. Using 3.00 g of this aqueous solution of strontium nitrate in lieu of the aqueous solution of cobalt nitrate, a catalyst was prepared in otherwise the same manner as in Example 13. The composition of this catalyst was 14.3 mass % $W_{12}Sb_3Sr_2Ox/SA5218$.

EXAMPLE 21

As the source of La, an aqueous solution of lanthanum nitrate was prepared. Thus, 21.67 g of lanthanum nitrate.$6H_2O$ was dissolved in water to make 100 g, whereby an aqueous solution of lanthanum nitrate with a La concentration of 0.5 mmol/g was obtained. Using 6.00 g of this aqueous solution of lanthanum nitrate in lieu of the aqueous solution of cobalt nitrate, a catalyst was prepared in otherwise the same manner as in Example 13. The composition of this catalyst was 15.5 mass % $W_{12}Sb_3La_2Ox/SA5218$.

EXAMPLE 22

As the source of Cr, an aqueous solution of chromium nitrate was prepared. Thus, 20.03 g of chromium nitrate.$9H_2O$ was dissolved in water to make 50 g, whereby an aqueous solution of chromium nitrate with a Cr concentration of 1 mmol/g was obtained. Except that 0.45 g of this aqueous solution of chromium nitrate was added to the impregnating liquor used in Example 16, a catalyst was prepared in otherwise the same manner as in Example 16.

The composition of this catalyst was 16.9 mass % $W_{12}Sb_3Zn_6Cr_{0.3}Ox/SA5218$.

EXAMPLE 23

Except that the reactant gas feeding rate was adjusted to 1.95 L (normal state)/min and the reaction temperature to 570° C., the reaction was conducted using the same catalyst as used in Example 22 under the same conditions as in Example 1. The results are shown in Table 1.

EXAMPLE 24

As the source of V, an aqueous solution of ammonium metavanadate was prepared. Thus, 5.91 g of ammonium metavanadate was dissolved in water to make 50 g, whereby an aqueous solution of ammonium metavanadate with a V concentration of 1 mmol/g was obtained. Except that 0.15 g of this aqueous solution was added to the impregnating liquor used in Example 16, the procedure of Example 16 was otherwise repeated to prepare a catalyst. The composition of this catalyst was 17.2 mass % $W_{12}Sb_3Zn_6V_{0.1}Ox/SA5218$.

EXAMPLE 25

Except that, 0.44 g of an aqueous solution of titanium tetrachloride (containing 16.0 to 17.0% of Ti) was added to the impregnating liquor used in Example 16, a catalyst was prepared in otherwise the same manner as in Example 16. The composition of this catalyst was 16.8 mass % $W_{12}Sb_3Zn_6Ti_1Ox/SA5218$.

EXAMPLE 26

Except that 20 g of a calcined silicon carbide carrier (5 mm sphere) was used in lieu of the carrier SA5218, the procedure of Example 1 was repeated to prepare a catalyst. The composition of this catalyst was 13.6 mass % $W_{12}Sb_3Fe_2Ox/SiC$.

EXAMPLE 27

Except that the amount of the aqueous solution of antimony tartrate was altered to 12.00 g, that of the aqueous solution of iron nitrate to 4.00 g and that of the aqueous solution of ammonium metatungstate to 11.12 g and conducting the calcining operation in streams of 1% oxygen gas (the balance nitrogen), the procedure of Example 1 was otherwise repeated to prepare a catalyst. The composition of this catalyst was 18.0 mass % $W_{12}Sb_3Fe_2Ox/SA5218$.

EXAMPLE 28

Using a suspension obtained by using 1.166 g of antimony trioxide powder (purity 99.999%) in lieu of the aqueous solution of antimony tartrate as an impregnating liquor and nitrogen gas as the calcining atmosphere, the procedure of Example 27 was otherwise repeated to prepare a catalyst. The composition of this catalyst was 25.0 mass % $W_{12}Sb_4Fe_2Ox/SA5218$.

EXAMPLE 29

Except that 4.00 g of an aqueous solution of bismuth nitrate with a Bi concentration of 0.5 mmol/g was added to the impregnating liquor used in Example 28, the procedure of Example 28 was otherwise repeated to prepare a catalyst. The composition of this catalyst was 23.0 mass % $W_{12}Sb_4Bi_1Fe_2Ox/SA5218$.

EXAMPLE 30

As the source of Ce, an aqueous solution of cerium nitrate was prepared. Thus, 21.73 g of cerium nitrate.$6H_2O$ was dissolved in water to make 100 g, whereby an aqueous solution of cerium nitrate with a Ce concentration of 0.5 mmol/g was obtained. Except that 2.00 g of an aqueous solution of cerium nitrate was added to the impregnating liquor used in Example 28, the procedure of Example 28 was otherwise repeated to prepare a catalyst. The composition of this catalyst was 25.4 mass % $W_{12}Sb_4Fe_2Ce_{0.5}Ox/SA5218$.

EXAMPLE 31

Except that the use of the aqueous solution of iron nitrate was omitted, the procedure of Example 1 was otherwise repeated to prepare a catalyst. The composition of this catalyst was 13.8 mass % $W_{12}Sb_3Ox/SA5218$.

COMPARATIVE EXAMPLE 1

Using an impregnating liquor prepared by diluting 5.56 g of the aqueous solution of ammonium metatungstate alone with 8 ml of water, the procedure of Example 1 was otherwise repeated to prepare a catalyst. The composition of this catalyst was 12.0 mass % $WOx/SA5218$.

TABLE 1

| | Reaction temp. (°C.) | p-Xylene conversion (%) | Selectivity (%) | | One-pass yield (%) | |
|---|---|---|---|---|---|---|
| | | | TPAL | PTAL | TPAL | PTAL |
| Example | | | | | | |
| 1 | 550 | 90.9 | 62.6 | 8.3 | 59.6 | 7.5 |
| 2 | 550 | 88.4 | 61.0 | 7.2 | 53.9 | 6.4 |
| 3 | 525 | 92.5 | 48.2 | 6.6 | 44.6 | 6.1 |
| 4 | 500 | 89.0 | 46.4 | 6.5 | 41.3 | 5.8 |
| 5 | 550 | 89.0 | 48.2 | 6.0 | 42.9 | 5.3 |
| 6 | 545 | 93.4 | 63.6 | 5.6 | 59.4 | 5.2 |
| 7 | 550 | 60.9 | 68.3 | 9.2 | 41.6 | 5.6 |
| 8 | 525 | 94.1 | 59.6 | 6.0 | 56.1 | 5.6 |
| 9 | 500 | 96.8 | 39.7 | 3.6 | 38.4 | 3.5 |
| 10 | 550 | 50.8 | 52.7 | 13.2 | 26.8 | 6.7 |
| 11 | 525 | 74.8 | 22.2 | 6.1 | 16.6 | 1.2 |
| 12 | 550 | 90.7 | 63.5 | 6.7 | 57.4 | 6.1 |
| 13 | 550 | 89.5 | 55.3 | 6.7 | 49.5 | 6.0 |
| 14 | 580 | 92.8 | 66.6 | 5.9 | 61.8 | 5.5 |
| 15 | 570 | 94.8 | 56.1 | 4.7 | 53.2 | 4.5 |
| 16 | 580 | 49.6 | 73.6 | 8.5 | 36.5 | 4.2 |
| 17 | 580 | 93.6 | 61.4 | 4.0 | 57.5 | 3.7 |
| 18 | 580 | 74.2 | 69.7 | 8.3 | 51.7 | 6.2 |
| 19 | 580 | 60.8 | 60.1 | 7.3 | 36.5 | 4.4 |
| 20 | 580 | 77.7 | 63.2 | 5.2 | 49.2 | 4.0 |
| 21 | 580 | 56.5 | 57.3 | 4.8 | 32.4 | 2.7 |
| 22 | 550 | 91.5 | 64.1 | 6.0 | 58.7 | 5.4 |
| 23 | 570 | 94.0 | 65.8 | 4.9 | 61.9 | 4.6 |
| 24 | 570 | 93.0 | 61.7 | 5.4 | 57.4 | 5.0 |
| 25 | 580 | 91.7 | 58.4 | 4.1 | 53.5 | 3.7 |
| 26 | 500 | 85.5 | 52.2 | 11.2 | 44.6 | 9.6 |
| 27 | 550 | 88.1 | 71.3 | 3.9 | 62.8 | 3.2 |
| 28 | 580 | 89.1 | 68.1 | 3.4 | 60.6 | 3.0 |
| 29 | 550 | 96.2 | 62.7 | 4.0 | 60.3 | 3.8 |
| 30 | 570 | 92.2 | 65.8 | 3.7 | 60.7 | 3.4 |
| 31 | 550 | 44.3 | 63.9 | 7.8 | 28.3 | 3.5 |
| Compar. Ex. 1 | 550 | 15.5 | 51.0 | 14.1 | 7.9 | 2.2 |

TPAL: terephthalaldehyde, PTAL: p-tolualdehyde

EXAMPLE 32

Without use of a carrier, the same solution as used for impregnation Example 1 was directly concentrated to dryness on a water bath by heating with stirring on a water bath and dried at 120° C. for 16 hours. The residue was pulverized and compression-molded into pellets (5 mm in diameter×5 mm long) and the pellets were calcined in the atmospheric air at 650° C. for 2 hours. The composition of the catalyst thus obtained was $W_{12}Sb_3Fe_2Ox$. Using 10 g of this catalyst, a reactant gas feeding rate of 6.00 L(normal state)/min (SV 42600 $hr^{-1}$) and a reaction temperature of 510° C., the reaction was carried out under otherwise the same conditions as in Example 1. The results were: p-xylene conversion 93.1%; selectivity for terephthalaldehyde 57.7%, selectivity for p-tolualdehyde 5.4%, one-pass yield of terephthalaldehyde 53.7%; one-pass yield of p-tolualdehyde 5.0%.

EXAMPLE 33

The exit gas during the 8 to 10 hour after the start of reaction in Example 1 was trapped in cold methanol. The trapped gas was concentrated in an evaporator to give 75 g of amethanolic solution. This solution contained 4.06 g terephthalaldehyde and 0.44 g of p-tolualdehyde.

An autoclave was charged with the above solution and 1 g of ruthenium-on-carbon (ruthenium content 5 mass %) and hermetically closed. After nitrogen purging, the autoclave was filled with hydrogen gas up to an internal pressure of 5 MPa and then heated at 80° C. The reaction was conducted under stirring until no more hydrogen was adsorbed (until the internal pressure ceased to drop).

After completion of the reaction, the contents were withdrawn, filtered and analyzed by gas chromatography. The results indicated that the above reaction mixture contained 3.85 g of 1,4-cyclohexanedimethanol and the conversion of terephthalaldehyde was 100%. Therefore, the yield of the 1,4-cyclohexanedimethanol was 89 mole % based on terephthalaldehyde. Production of 4% p-xylylene glycol was noted.

EXAMPLE 34

The exit gas during the 8 to 10 hour after the start of reaction in Example 6 was trapped in cold methanol and concentrated in an evaporator to give 75 g of a methanolic solution. This solution contained 4.25 g of terephthalaldehyde and 0.32 g of p-tolualdehyde.

An autoclave was charged with the above solution and 1 g of Raney nickel (nickel content 93~95 mass %, aluminum content 5 to 7 mass %) and hermetically closed. After nitrogen purging, the autoclave was filled with hydrogen gas up to an internal pressure of 4 MPa and heated at 60° C. The reaction was carried out under stirring until the absorption of hydrogen gas had ceased (until the internal pressure had ceased to drop).

After completion of the reaction, the contents were withdrawn, filtered, and analyzed by gas chromatography. The results indicated that this reaction mixture contained 3.97 g of 1,4-cyclohexanedimethanol and the conversion of terephthalaldehyde was 100%. Therefore, the yield of the 1,4-cyclohexanedimethanol was 87 mole % based on terephthalaldehyde. Production of 5% p-xylylene glycol was noted.

COMPARATIVE EXAMPLE 2

The exit gas in Comparative Example 1 was trapped in the same manner as in Example 1 and prepared into 75 g of a methanolic solution. This solution contained 0.56 g of terephthalaldehyde and 0.14 g of p-tolualdehyde.

The hydrogenation reaction was carried out under the same conditions as in Example 1. As a result, the yield of 1,4-cyclohexanedimethanol was 56% based on the terephthalaldehyde charge.

What is claimed is:

1. A catalyst for oxidation of a methylbenzene which is used for the production of the corresponding aromatic aldehyde by the gas-phase oxidation of a methylbenzene in the presence of molecular oxygen, and has a composition of the following general formula (1):

$$WaXbYcOx \qquad (1)$$

wherein W represents a tungsten atom; X represents Sb; Y represents at least one element selected from the group consisting of Fe, Co, Ni, Mn, Re, Cr, V, Nb, Ti, Zr, Zn, Cd, Y, La, Ce, B, Al, Tl, Sn, Mg, Ca, Sr, Ba, Li, Na, K, Rb and Cs; O represents an oxygen atom; a, b, c and x represent the numbers of atoms of W, X, Y and O, respectively; provided, however, the proportions of a, b and c are such that when a=12, b=0.5 to 10 and c=0 to 15; x represents a numerical value determined by the oxidized states of the elements other than oxygen.

2. The catalyst for oxidzation of a methylbenzene according to claim 1 as supported on a fire-resistant inorganic carrier.

3. The catalyst for oxidation of a methylbenzene according to claim 1 as supported on a fire-resistant inorganic carrier wherein the fire-resistant inorganic carrier is α-alumina or silicon carbide.

4. The catalyst for oxidation of a methylbenzene according to claim 1 wherein said methylbenzene contains 8 to 10 carbon atoms.

5. The catalyst for oxidation of a methylbenzene according to claim 1 wherein said methylbenzene is p-xylene.

6. A process for producing an aromatic aldehyde comprising gas-phase oxidation of the corresponding methylbenzene in the presence of molecular oxygen, wherein the catalyst for oxidation of a methylbenzene according to claim 1 is used.

7. A process for producing an aromatic aldehyde comprising gas-phase oxidation of the corresponding methylbenzene in the presence of molecular oxygen, wherein the catalyst for oxidation of a methylbenzene according to claim 1 is used and the corresponding methylbenzene contains 8 to 10 carbon atoms.

8. A process for producing an aromatic aldehyde which comprises gas-phase oxidation of p-xylene using the catalyst for oxidation of a methylbenzene according to claim 1 in the presence of molecular oxygen to thereby give the corresponding terephthalaldehyde.

9. A process for producing cyclohexanedimethanol which comprises obtaining a phthalaldehyde by the process for producing the corresponding aromatic aldehyde by gas-phase oxidation of xylene and hydrogenating a phthalaldehyde, said oxidation being carried out using the catalyst for oxidation of a methylbenzene according to claim 1 in the presence of molecular oxygen.

10. A process for producing 1,4-cyclohexanedimethanol which comprises obtaining a terephthalaldehyde by the process for producing the corresponding aromatic aldehyde by gas-phase oxidation of p-xylene and hydrogenating a terephthalaldehyde, said gas-phase oxidation being carried out using the catalyst for oxidation of a methylbenzene according to claim 1 in the presence of molecular oxygen.

* * * * *